(12) United States Patent  
Al-Ali

(10) Patent No.: US 7,844,315 B2
(45) Date of Patent: Nov. 30, 2010

(54) PHYSIOLOGICAL MEASUREMENT COMMUNICATIONS ADAPTER

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 1156 days.

(21) Appl. No.: 11/417,006

(22) Filed: May 3, 2006

(65) Prior Publication Data

US 2007/0173701 A1 Jul. 26, 2007

Related U.S. Application Data

(63) Continuation of application No. 11/048,330, filed on Feb. 1, 2005, which is a continuation of application No. 10/377,933, filed on Feb. 28, 2003, now Pat. No. 6,850,788.

(60) Provisional application No. 60/367,428, filed on Mar. 25, 2002.

(51) Int. Cl.
*A61B 5/1455* (2006.01)
*A61B 5/00* (2006.01)

(52) U.S. Cl. .................. 600/323; 600/300; 600/502; 128/903

(58) Field of Classification Search ........... 600/310, 600/322, 323, 300, 504, 505, 506, 507; 128/903
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |

(Continued)

*Primary Examiner*—Eric F Winakur
(74) *Attorney, Agent, or Firm*—Knobbe, Martens, Olson & Bear LLP

(57) ABSTRACT

A sensor signal is input at a patient location and a physiological waveform responsive to the sensor signal is generated. The physiological waveform is wirelessly communicated from the patient location to a monitor location. The physiological waveform is adapted to a particular patient monitor at the monitor location. The adapted physiological waveform is output to a sensor port of the patient monitor. Accordingly, the patient monitor derives physiological measurements from the adapted physiological waveform that are generally equivalent to measurements derivable from the physiological waveform by a monitor compatible with the sensor signal.

11 Claims, 17 Drawing Sheets

U.S. PATENT DOCUMENTS

| | | |
|---|---|---|
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A * | 12/2000 | Schmidt et al. ........ 340/870.01 |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 * | 10/2002 | Boesen ........................ 128/903 |
| 6,501,975 B2 | 12/2002 | Diab et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,897,788 B2 * | 5/2005 | Khair et al. ................. 128/903 |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |

* cited by examiner

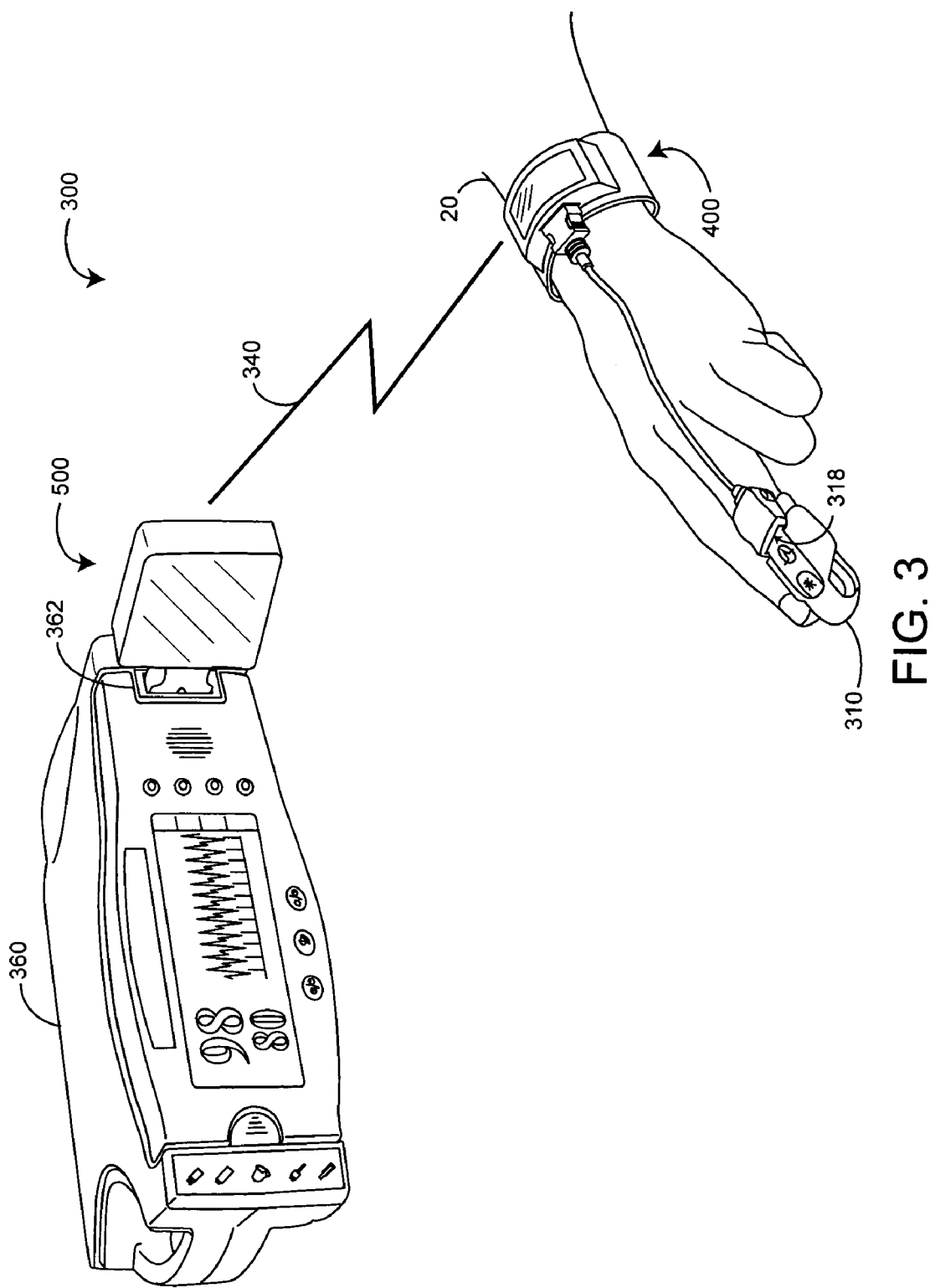

PHYSIOLOGICAL MEASUREMENT COMMUNICATIONS ADAPTER

CROSS-REFERENCE TO RELATED APPLICATIONS

The present application claims priority benefit under 35 U.S.C. §120 to, and is a continuation of, U.S. patent application Ser. No. 11/048,330, filed Feb. 1, 2005 entitled "Physiological Measurement Communications Adapter," which is a continuation of application Ser. No. 10/377,933, filed Feb. 28, 2003, now U.S. Pat. No. 6,850,788, entitled "Physiological Measurement Communications Adapter," which claims priority benefit under 35 U.S.C. §119(e) from U.S. Provisional Application No. 60/367,428, filed Mar. 25, 2002, entitled "Physiological Measurement Communications Adapter." The present application also incorporates the foregoing utility disclosures herein by reference.

BACKGROUND OF THE INVENTION

Patient vital sign monitoring may include measurements of blood oxygen, blood pressure, respiratory gas, and EKG among other parameters. Each of these physiological parameters typically require a sensor in contact with a patient and a cable connecting the sensor to a monitoring device. For example, FIGS. 1-2 illustrate a conventional pulse oximetry system 100 used for the measurement of blood oxygen. As shown in FIG. 1, a pulse oximetry system has a sensor 110, a patient cable 140 and a monitor 160. The sensor 110 is typically attached to a finger 10 as shown. The sensor 110 has a plug 118 that inserts into a patient cable socket 142. The monitor 160 has a socket 162 that accepts a patient cable plug 144. The patient cable 140 transmits an LED drive signal 252 (FIG. 2) from the monitor 160 to the sensor 110 and a resulting detector signal 254 (FIG. 2) from the sensor 110 to the monitor 160. The monitor 160 processes the detector signal 254 (FIG. 2) to provide, typically, a numerical readout of the patient's oxygen saturation, a numerical readout of pulse rate, and an audible indicator or "beep" that occurs in response to each arterial pulse.

As shown in FIG. 2, the sensor 110 has both red and infrared LED emitters 212 and a photodiode detector 214. The monitor 160 has a sensor interface 271, a signal processor 273, a controller 275, output drivers 276, a display and audible indicator 278, and a keypad 279. The monitor 160 determines oxygen saturation by computing the differential absorption by arterial blood of the two wavelengths emitted by the sensor emitters 212, as is well-known in the art. The sensor interface 271 provides LED drive current 252 which alternately activates the red and IR LED emitters 212. The photodiode detector 214 generates a signal 254 corresponding to the red and infrared light energy attenuated from transmission through the patient finger 10 (FIG. 1). The sensor interface 271 also has input circuitry for amplification, filtering and digitization of the detector signal 254. The signal processor 273 calculates a ratio of detected red and infrared intensities, and an arterial oxygen saturation value is empirically determined based on that ratio. The controller 275 provides hardware and software interfaces for managing the display and audible indicator 278 and keypad 279. The display and audible indicator 278 shows the computed oxygen status, as described above, and provides the pulse beep as well as alarms indicating oxygen desaturation events. The keypad 279 provides a user interface for setting alarm thresholds, alarm enablement, and display options, to name a few.

SUMMARY OF THE INVENTION

Conventional physiological measurement systems are limited by the patient cable connection between sensor and monitor. A patient must be located in the immediate vicinity of the monitor. Also, patient relocation requires either disconnection of monitoring equipment and a corresponding loss of measurements or an awkward simultaneous movement of patient equipment and cables. Various devices have been proposed or implemented to provide wireless communication links between sensors and monitors, freeing patients from the patient cable tether. These devices, however, are incapable of working with the large installed base of existing monitors and sensors, requiring caregivers and medical institutions to suffer expensive wireless upgrades. It is desirable, therefore, to provide a communications adapter that is plug-compatible both with existing sensors and monitors and that implements a wireless link replacement for the patient cable.

One aspect of a physiological measurement communications adapter is a sensor signal input at a patient location. A physiological waveform responsive to the sensor signal is generated. The physiological waveform is wirelessly communicated from the patient location to a monitor location. The physiological waveform is adapted to a particular patient monitor at the monitor location. The adapted physiological waveform is output to a sensor port of the patient monitor. Accordingly, the patient monitor derives physiological measurements from the adapted physiological waveform that are generally equivalent to measurements derivable from the physiological waveform by a monitor compatible with the sensor signal.

Another aspect of a physiological measurement communications adapter is an input sensor signal at a patient location. A physiological waveform responsive to the sensor signal is generated. The sample rate of the physiological waveform is reduced, and the reduced sample rate physiological waveform is wirelessly transmitted from the patient location to a monitor location. The reduced sample rate physiological waveform is adapted to a particular patient monitor at the monitor location. The adapted physiological waveform is output to a sensor port of the patient monitor so that the patient monitor derives physiological measurements from the adapted physiological waveform that are generally equivalent to measurements derivable from the physiological waveform by a monitor compatible with the sensor signal.

A further aspect of a physiological measurement communications adapter is a sensor interface means for inputting a sensor signal from a noninvasive sensor attached to a patient tissue site and a first processor means for generating a physiological waveform responsive to the sensor signal. The communications adapter also has a wireless communications means for communicating the physiological waveform from a patient location to a monitor location and a second processor means for adapting the physiological waveform to a particular monitor at the monitor location. In addition, the communications adapter has a monitor interface means for outputting the adapted physiological waveform to a sensor port of the monitor.

BRIEF DESCRIPTION OF THE DRAWINGS

FIG. 3 is an illustration of a physiological measurement communications adapter;

DETAILED DESCRIPTION OF THE PREFERRED EMBODIMENTS

Overview

Figure 4A:
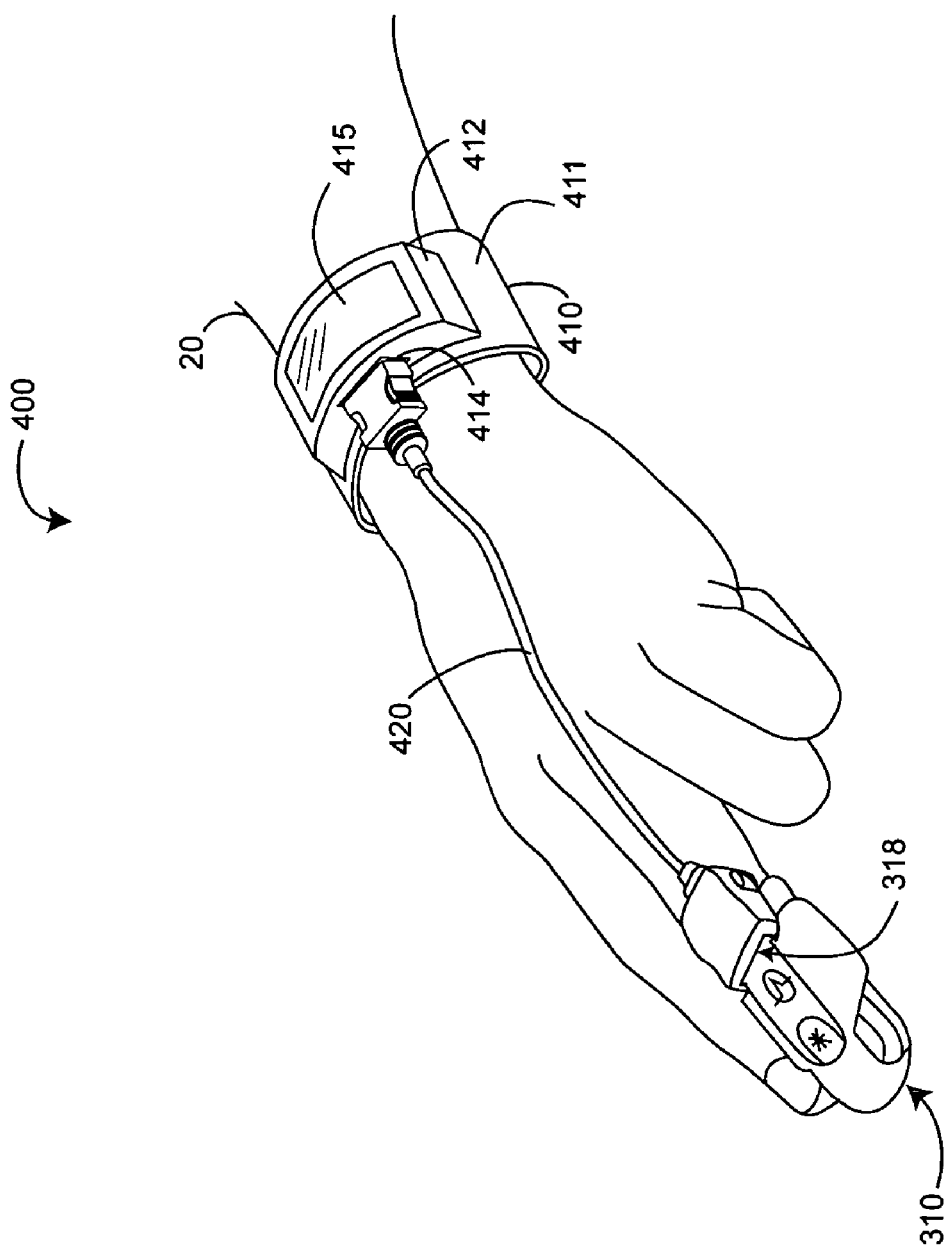
FIGS. 4A-B are illustrations of communications adapter sensor modules.
Figure 4B:
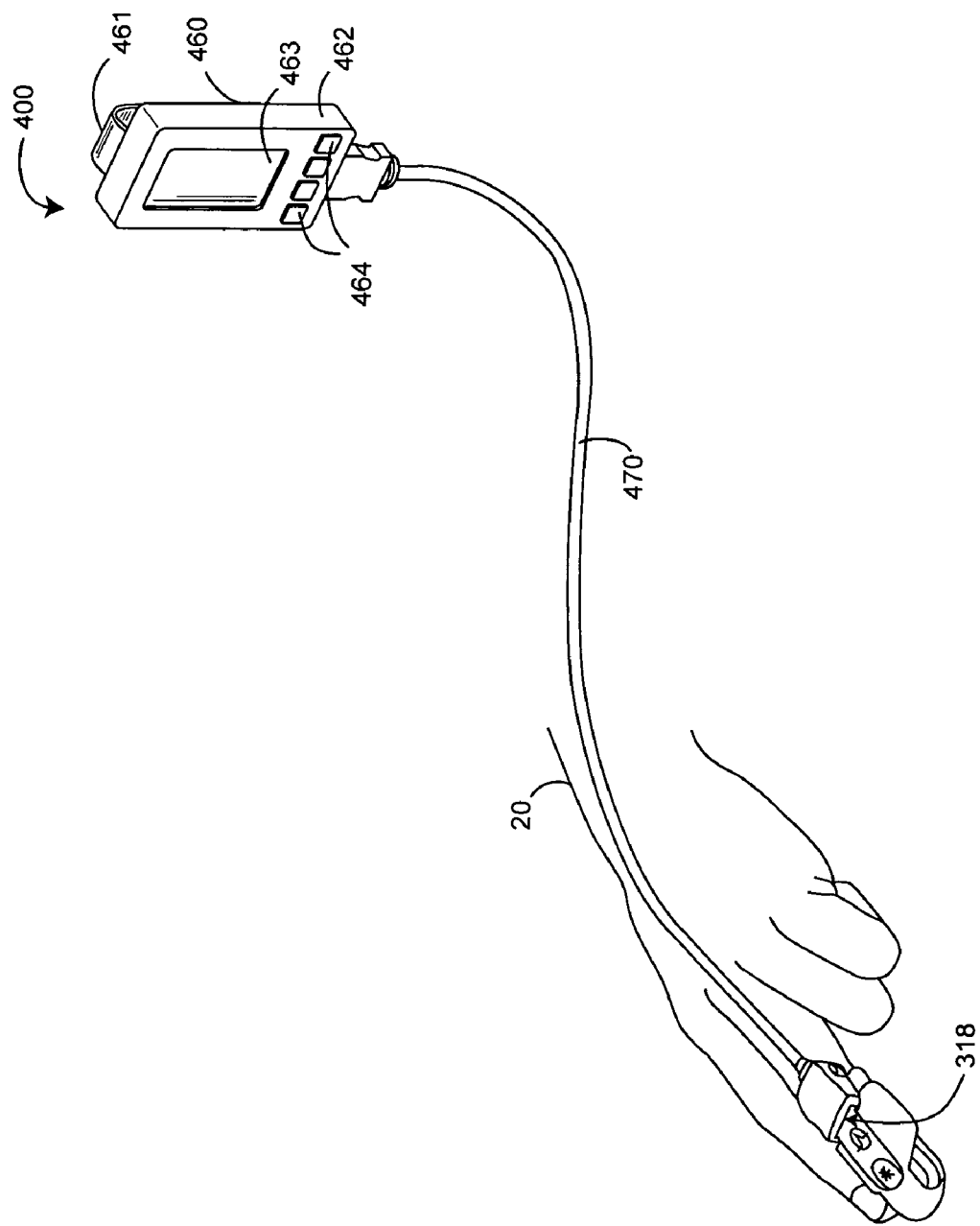
Figure 5A:
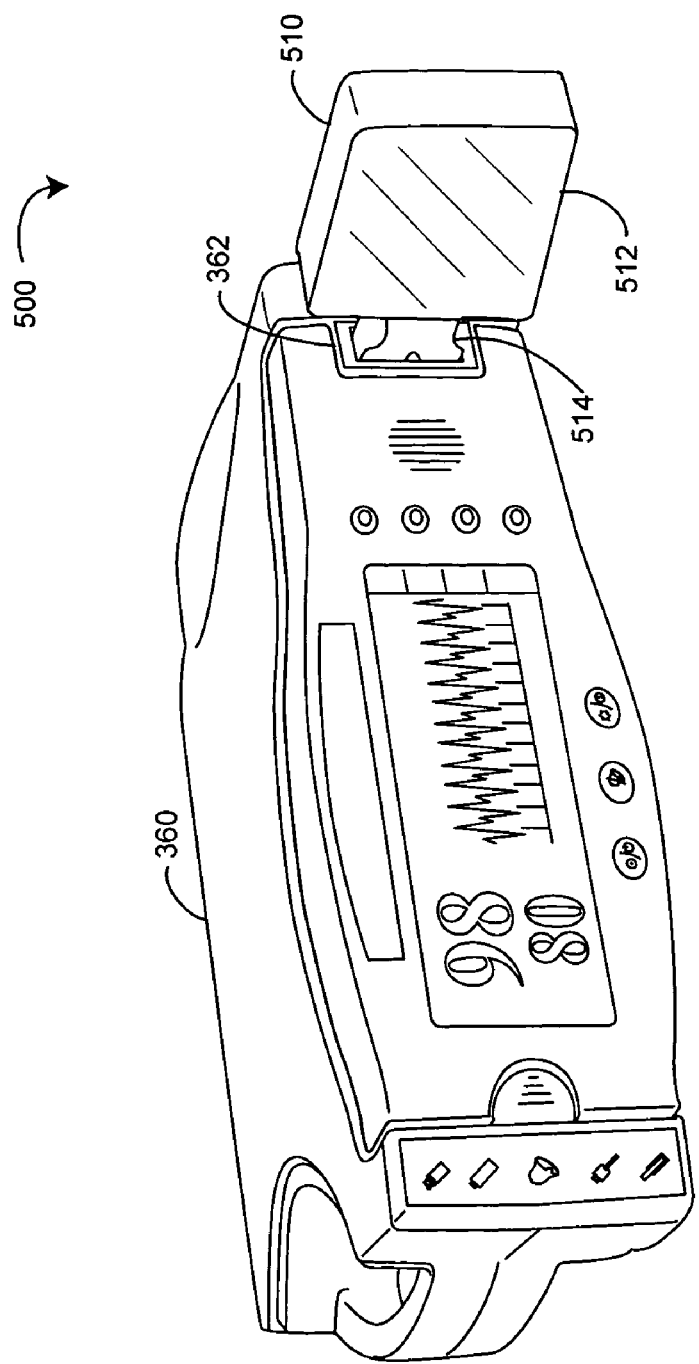
FIGS. 5A-C are illustrations of communications adapter monitor modules.
Figure 5B:
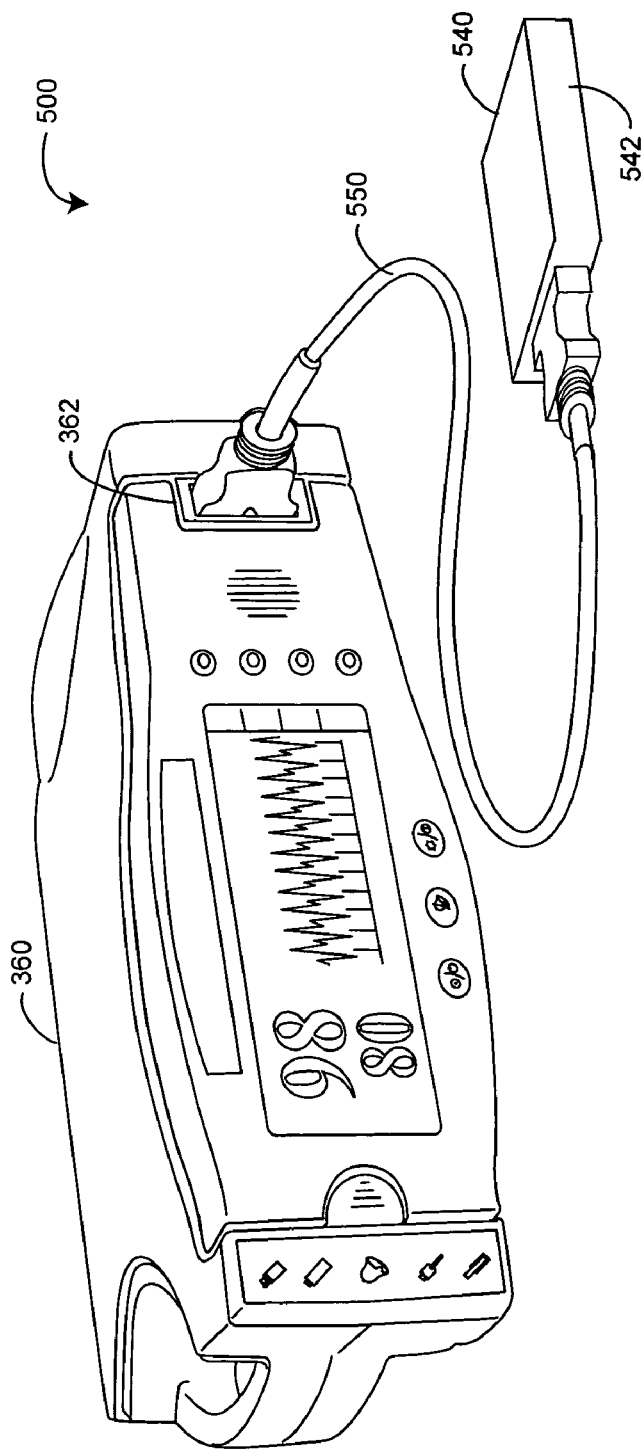
Figure 5C:
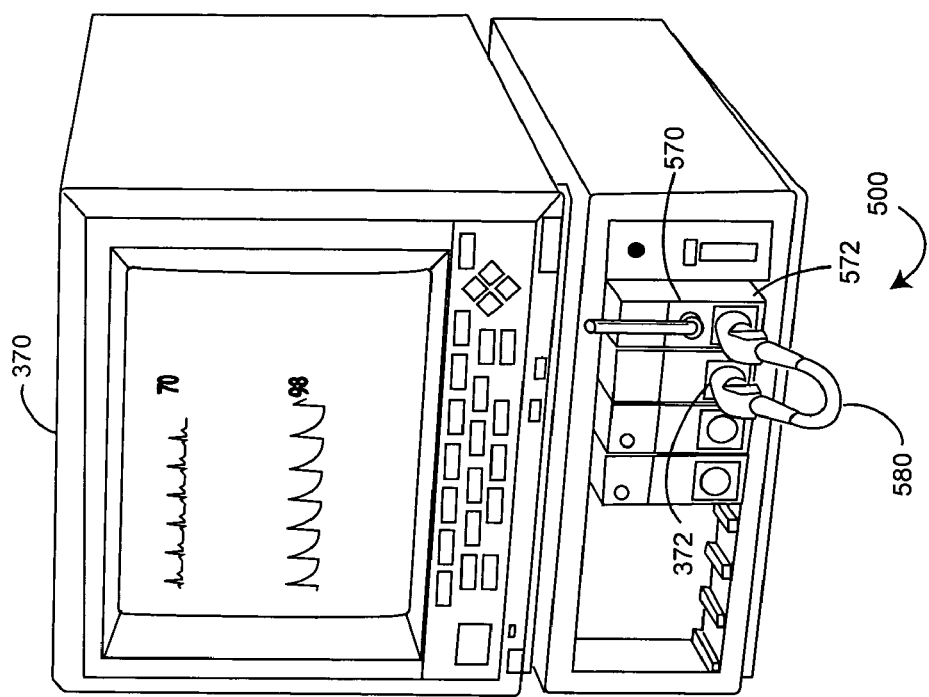
Figure 6:
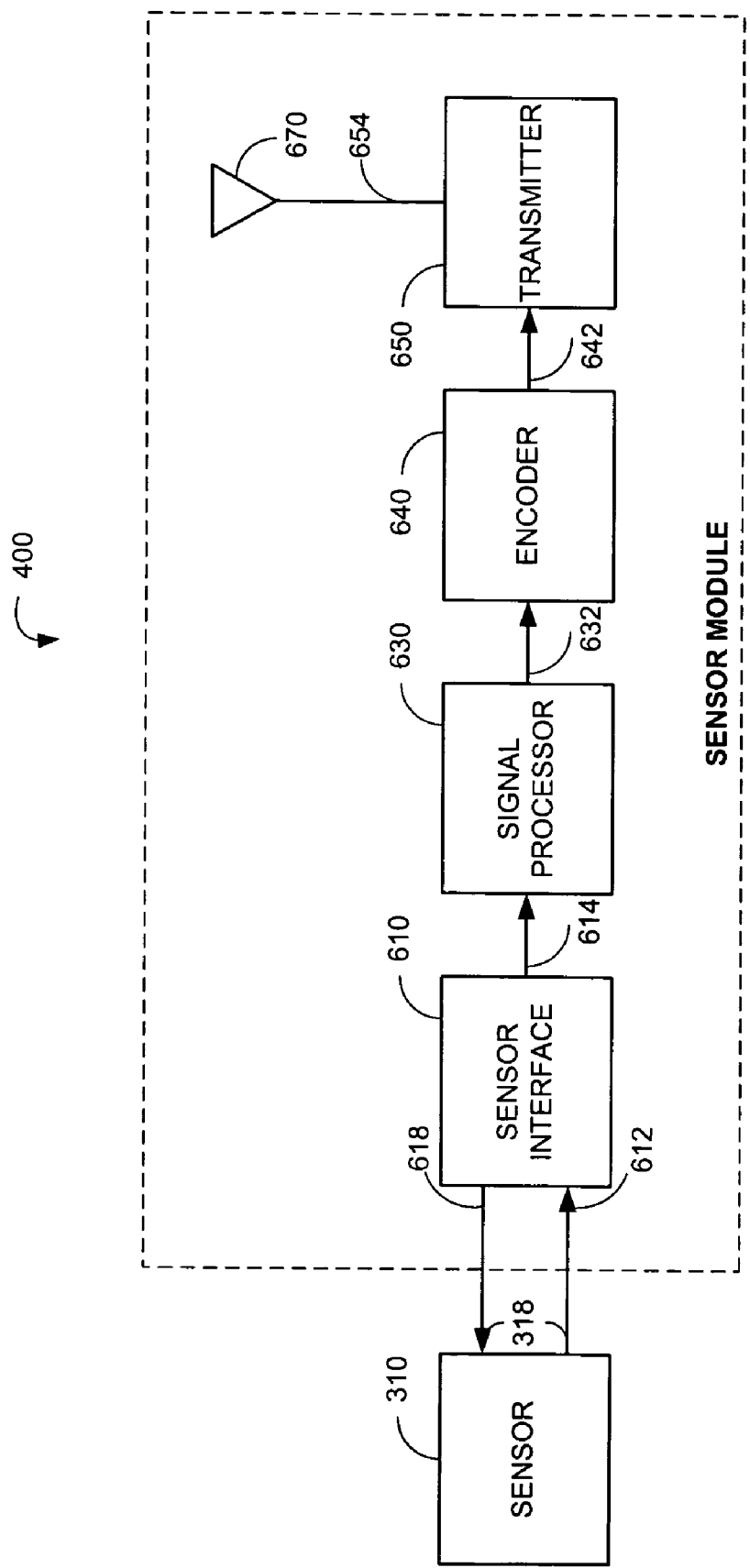
FIG. 6 is a functional block diagram of a communications adapter sensor module.
Figure 7:
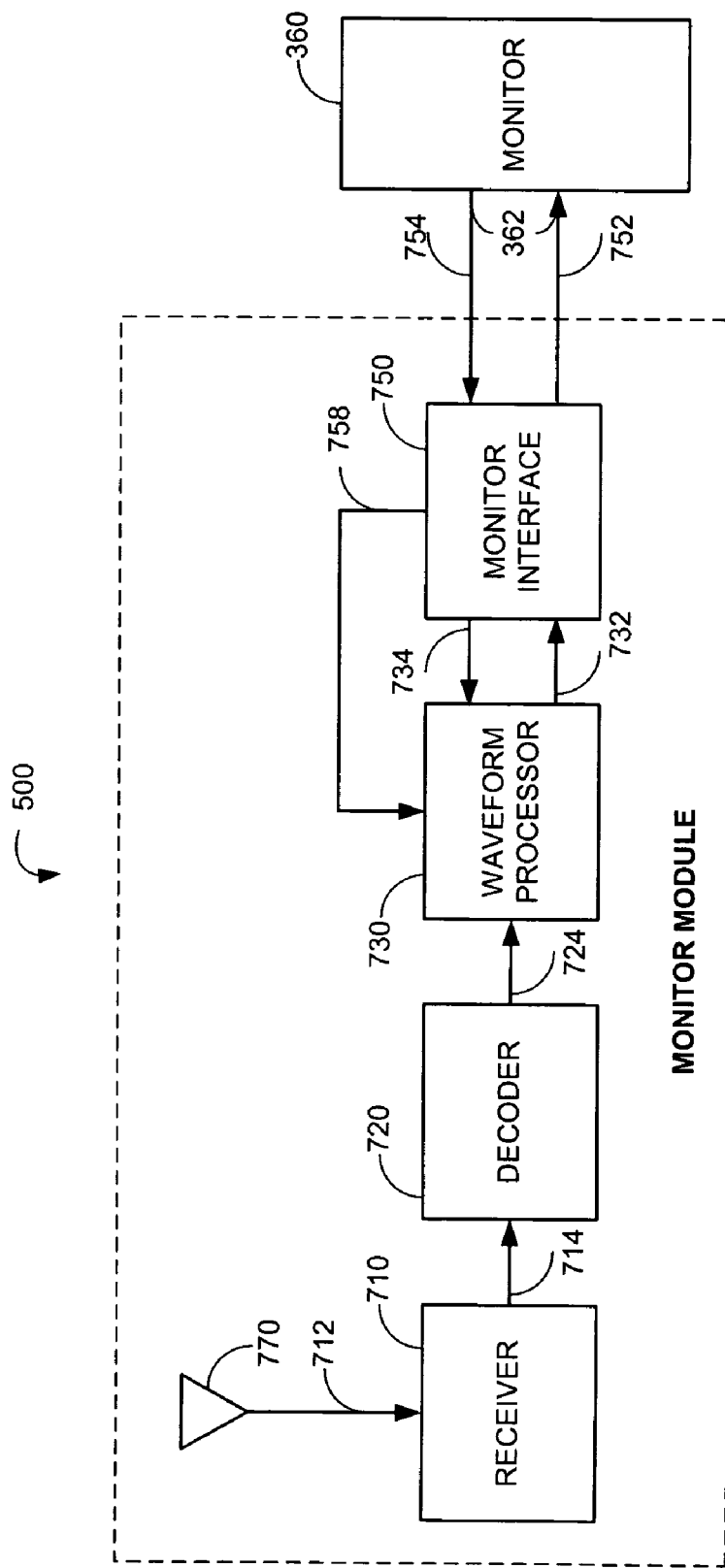
FIG. 7 is a functional block diagram of a communications adapter monitor module.
Figure 8:
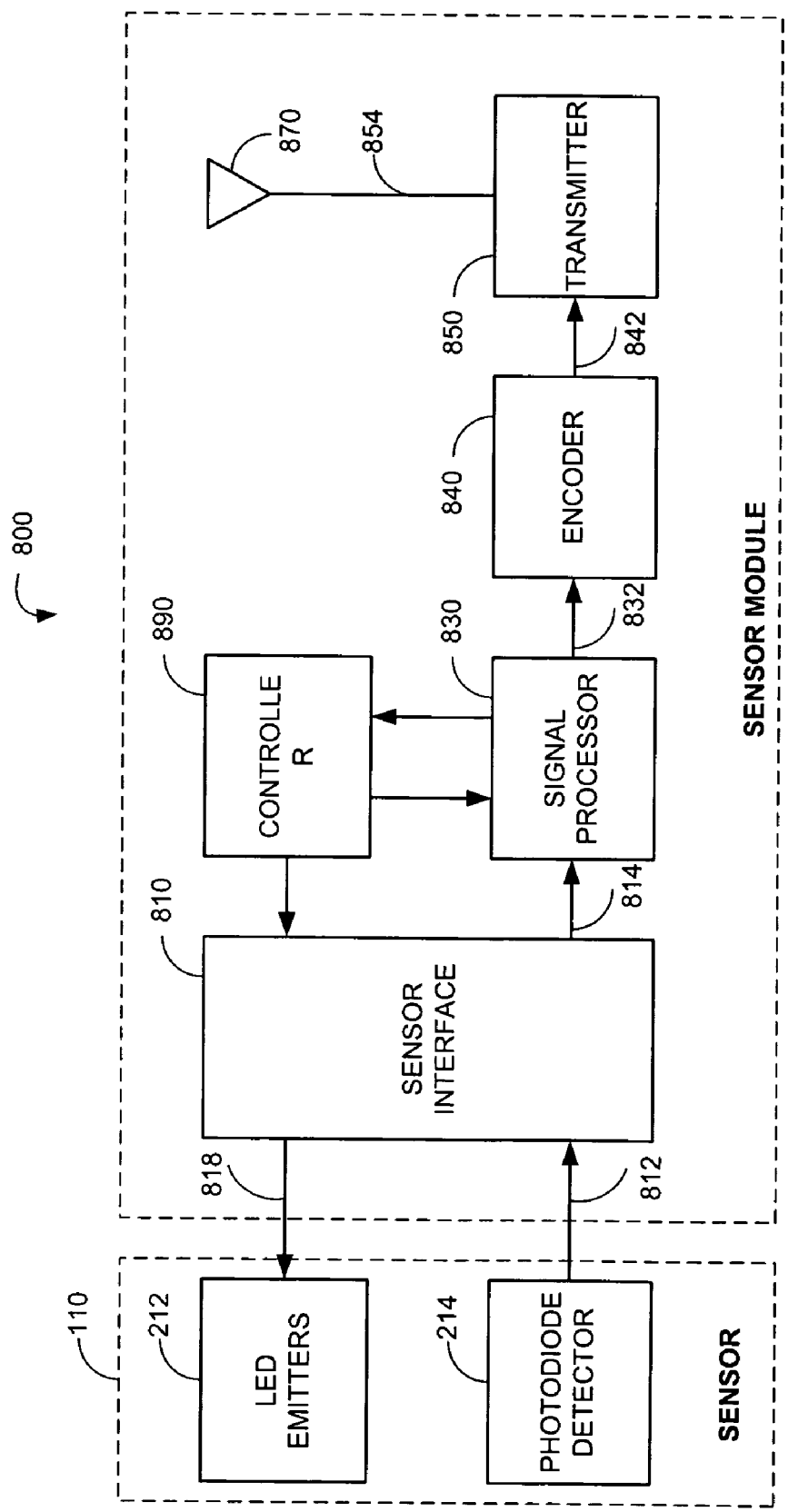
FIG. 8 is a functional block diagram of a sensor module configured to transmit measured pulse oximeter parameters.
Figure 9:
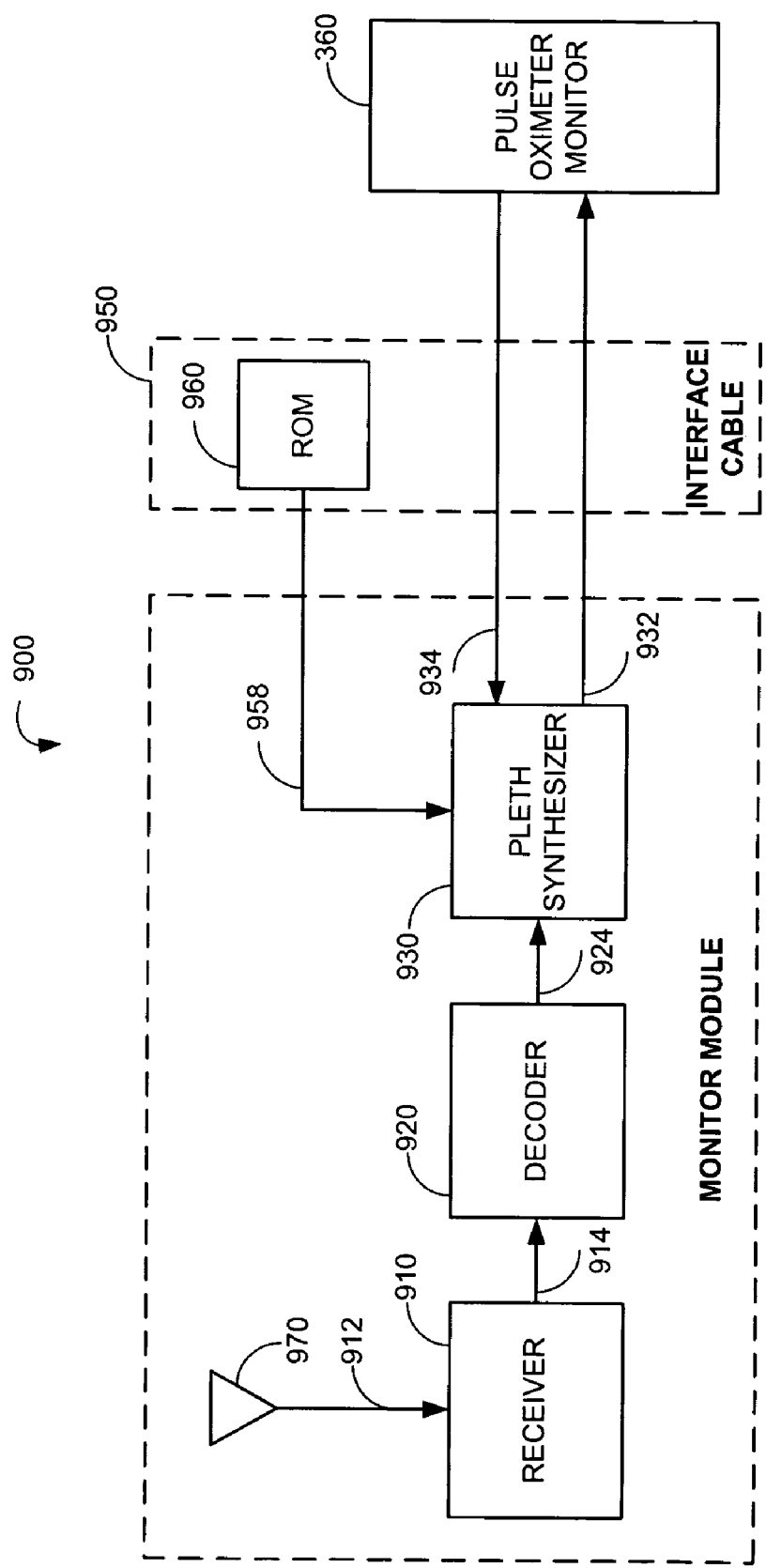
FIG. 9 is a functional block diagram of a monitor module configured to received measured pulse oximeter parameters.
Figure 13:
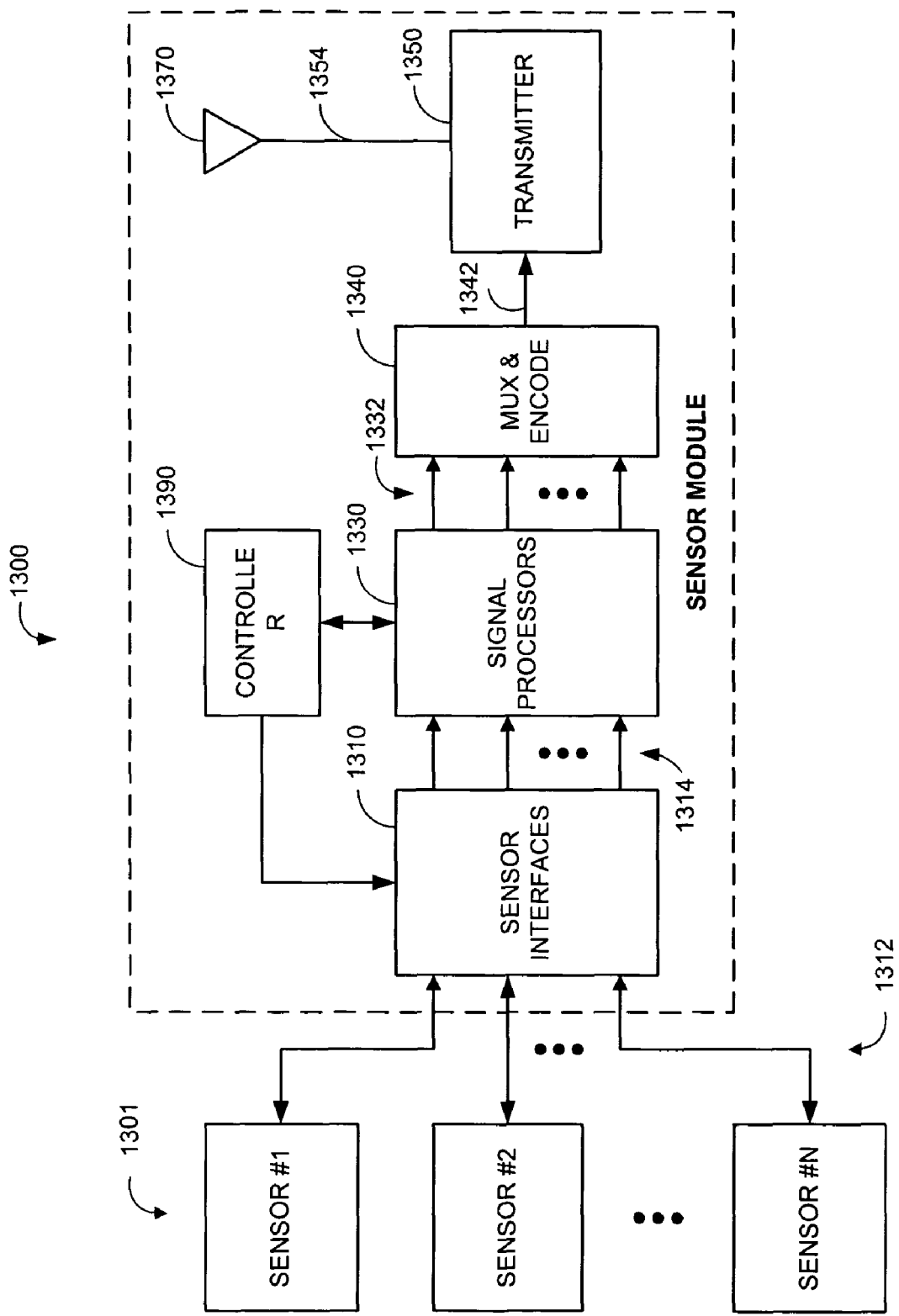
FIG. 13 is a functional block diagram of a sensor module configured for multiple sensors.
Figure 14:
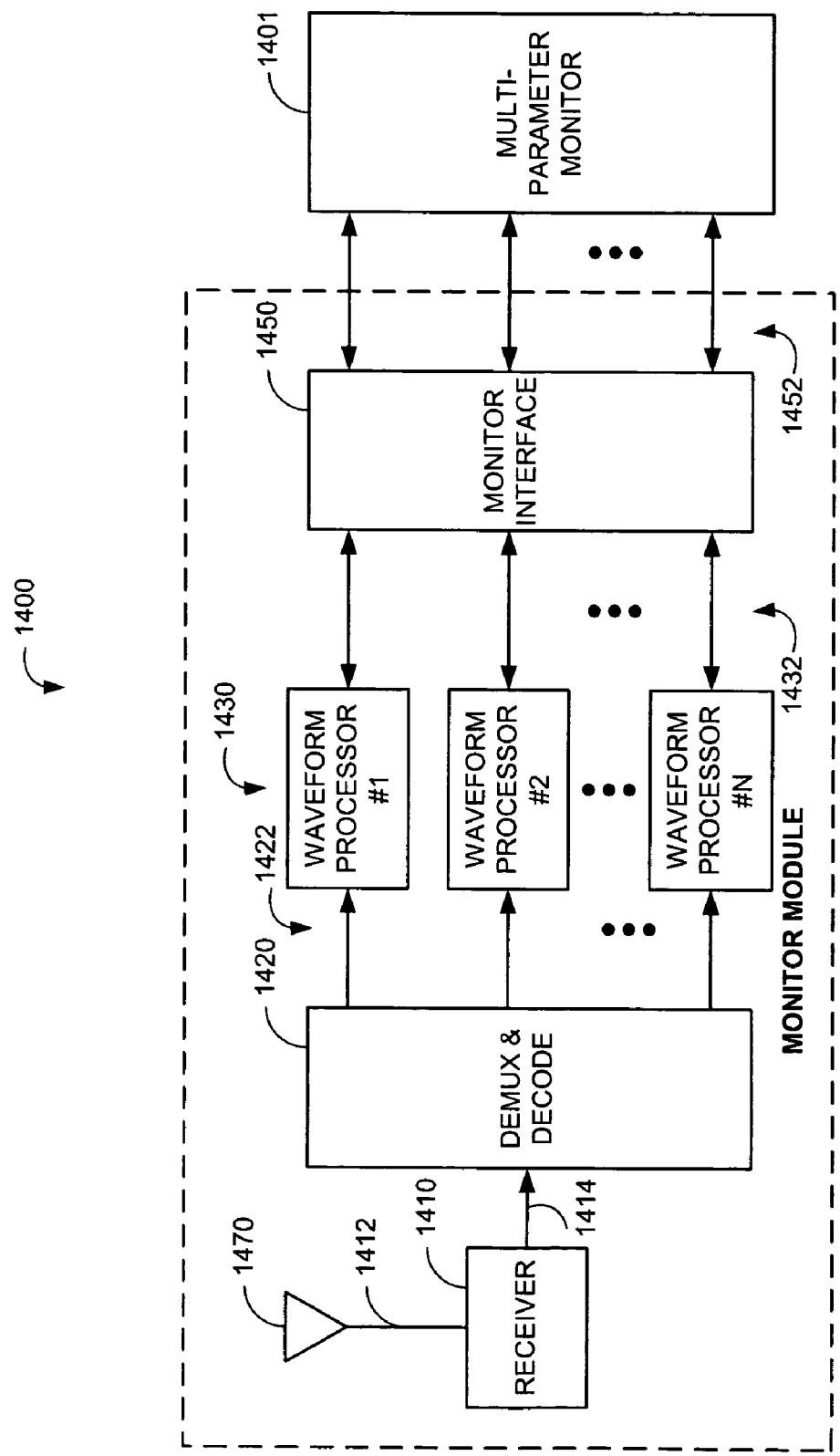
FIG. 14 is a functional block diagram of a monitor module configured for multiple sensors.

FIG. 3 illustrates one embodiment of a communications adapter. FIGS. 4-5 illustrate physical configurations for a communications adapter. In particular, FIGS. 4A-B illustrate sensor module configurations and FIGS. 5A-C illustrate monitor module configurations. FIGS. 6-14 illustrate communications adapter functions. In particular, FIGS. 6-7 illustrate general functions for a sensor module and a monitor module, respectively. FIGS. 8-9 functionally illustrate a communications adapter where derived pulse oximetry parameters, such as saturation and pulse rate are transmitted between a sensor module and a monitor module. Also, FIGS. 10-12 functionally illustrate a communications adapter where a plethysmograph is transmitted between a sensor module and a monitor module. FIGS. 13-14 functionally illustrate a multiple-parameter communications adapter.

Figure 1:
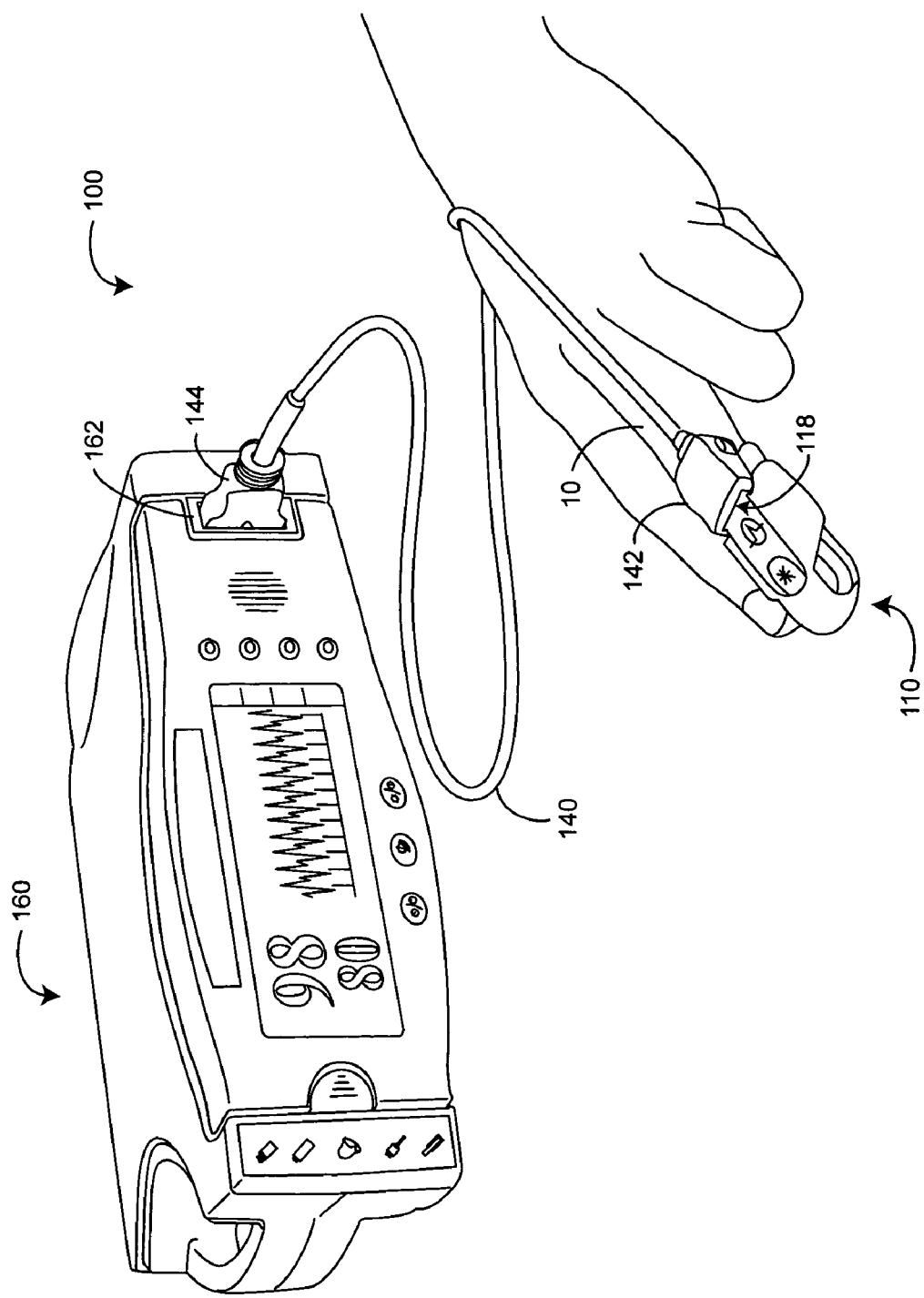
FIG. 1 is an illustration of a prior art pulse oximetry system.

FIG. 3 illustrates a communications adapter 300 having a sensor module 400 and a monitor module 500. The communications adapter 300 communicates patient data derived from a sensor 310 between the sensor module 400, which is located proximate a patient 20 and the monitor module 500, which is located proximate a monitor 360. A wireless link 340 is provided between the sensor module 400 and the monitor module 500, replacing the conventional patient cable, such as a pulse oximetry patient cable 140 (FIG. 1). Advantageously, the sensor module 400 is plug-compatible with a conventional sensor 310. In particular, the sensor connector 318 connects to the sensor module 400 in a similar manner as to a patient cable. Further, the sensor module 400 outputs a drive signal to the sensor 310 and inputs a sensor signal from the sensor 310 in an equivalent manner as a conventional monitor 360. The sensor module 400 may be battery powered or externally powered. External power may be for recharging internal batteries or for powering the sensor module during operation or both.

As shown in FIG. 3, the monitor module 500 is advantageously plug-compatible with a conventional monitor 360. In particular, the monitors sensor port 362 connects to the monitor module 500 in a similar manner as to a patient cable, such as a pulse oximetry patient cable 140 (FIG. 1). Further, the monitor module 500 inputs a drive signal from the monitor 360 and outputs a corresponding sensor signal to the monitor 360 in an equivalent manner as a conventional sensor 310. As such, the combination sensor module 400 and monitor module 500 provide a plug-compatible wireless replacement for a patient cable, adapting an existing wired physiological measurement system into a wireless physiological measurement system. The monitor module 500 may be battery powered, powered from the monitor, such as by tapping current from a monitor's LED drive, or externally powered from an independent AC or DC power source.

Although a communications adapter 300 is described herein with respect to a pulse oximetry sensor and monitor, one of ordinary skill in the art will recognize that a communications adapter may provide a plug-compatible wireless replace for a patient cable that connects any physiological sensor and corresponding monitor. For example, a communications adapter 300 may be applied to a biopotential sensor, a non-invasive blood pressure (NIBP) sensor, a respiratory rate sensor, a glucose sensor and the corresponding monitors, to name a few.

Sensor Module Physical Configurations

FIGS. 4A-B illustrate physical embodiments of a sensor module 400. FIG. 4A illustrates a wrist-mounted module 410 having a wrist strap 411, a case 412 and an auxiliary cable 420. The case 412 contains the sensor module electronics, which are functionally described with respect to FIG. 6, below. The case 412 is mounted to the wrist strap 411, which attaches the wrist-mounted module 410 to a patient 20. The auxiliary cable 420 mates to a sensor connector 318 and a module connector 414, providing a wired link between a conventional sensor 310 and the wrist-mounted module 410. Alternatively, the auxiliary cable 420 is directly wired to the sensor module 400. The wrist-mounted module 410 may have a display 415 that shows sensor measurements, module status and other visual indicators, such as monitor status. The wrist-mounted module 410 may also have keys (not shown) or other input mechanisms to control its operational mode and characteristics. In an alternative embodiment, the sensor 310 may have a tail (not shown) that connects directly to the wrist-mounted module 410, eliminating the auxiliary cable 420.

FIG. 4B illustrates a clip-on module 460 having a clip 461, a case 462 and an auxiliary cable 470. The clip 461 attaches the clip-on module 460 to patient clothing or objects near a patient 20, such as a bed frame. The auxiliary cable 470 mates to the sensor connector 318 and functions as for the auxiliary cable 420 (FIG. 4A) of the wrist-mounted module 410 (FIG. 4A), described above. The clip-on module 460 may have a display 463 and keys 464 as for the wrist-mounted module 410 (FIG. 4A). Either the wrist-mounted module 410 or the clip-on module 460 may have other input or output ports (not shown) that download software, configure the module, or provide a wired connection to other measurement instruments or computing devices, to name a few examples.

Monitor Module Physical Configurations

FIGS. 5A-C illustrate physical embodiments of a monitor module 500. FIG. 5A illustrates a direct-connect module 510 having a case 512 and an integrated monitor connector 514. The case 512 contains the monitor module electronics, which are functionally described with respect to FIG. 7, below. The monitor connector 514 mimics that of the monitor end of a patient cable, such as a pulse oximetry patient cable 140 (FIG. 1), and electrically and mechanically connects the monitor module 510 to the monitor 360 via the monitor's sensor port 362.

FIG. 5B illustrates a cable-connect module 540 having a case 542 and an auxiliary cable 550. The case 542 functions as for the direct-connect module 510 (FIG. 5A), described above. Instead of directly plugging into the monitor 360, the cable-connect module 540 utilizes the auxiliary cable 550, which mimics the monitor end of a patient cable, such as a pulse oximetry patient cable 140 (FIG. 1), and electrically connects the cable-connect module 540 to the monitor sensor port 362.

FIG. 5C illustrates a plug-in module 570 having a plug-in case 572 and an auxiliary cable 580. The plug-in case 572 is mechanically compatible with the plug-in chassis of a multi-parameter monitor 370 and may or may not electrically connect to the chassis backplane. The auxiliary cable 580 mimics a patient cable and electrically connects the plug-in module 570 to the sensor port 372 of another plug-in device. A direct-connect module 510 (FIG. 5A) or a cable-connect module 540 (FIG. 5B) may also be used with a multiparameter monitor 370.

In a multiparameter embodiment, such as described with respect to FIGS. 13-14, below, a monitor module 500 may connect to multiple plug-in devices of a multiparameter monitor 370. For example, a cable-connect module 540 (FIG. 5B) may have multiple auxiliary cables 550 (FIG. 5B) that connect to multiple plug-in devices installed within a multi-parameter monitor chassis. Similarly, a plug-in module 570 may have one or more auxiliary cables 580 with multiple connectors for attaching to the sensor ports 372 of multiple plug-in devices.

Communications Adapter Functions

FIGS. 6-7 illustrate functional embodiments of a communications adapter. FIG. 6 illustrates a sensor module 400 having a sensor interface 610, a signal processor 630, an encoder 640, a transmitter 650 and a transmitting antenna 670. A physiological sensor 310 provides an input sensor signal 612 at the sensor connector 318. Depending on the sensor 310, the sensor module 400 may provide one or more drive signals 618 to the sensor 310. The sensor interface 610 inputs the sensor signal 612 and outputs a conditioned signal 614. The conditioned signal 614 may be coupled to the transmitter 650 or further processed by a signal processor 630. If the sensor module configuration utilizes a signal processor 630, it derives a parameter signal 632 responsive to the sensor signal 612, which is then coupled to the transmitter 650. Regardless, the transmitter 650 inputs a baseband signal 642 that is responsive to the sensor signal 612. The transmitter 650 modulates the baseband signal 642 with a carrier to generate a transmit signal 654. The transmit signal 654 may be derived by various amplitude, frequency or phase modulation schemes, as is well known in the art. The transmit signal 654 is coupled to the transmit antenna 670, which provides wireless communications to a corresponding receive antenna 770 (FIG. 7), as described below.

As shown in FIG. 6, the sensor interface 610 conditions and digitizes the sensor signal 612 to generate the conditioned signal 614. Sensor signal conditioning may be performed in the analog domain or digital domain or both and may include amplification and filtering in the analog domain and filtering, buffering and data rate modification in the digital domain, to name a few. The resulting conditioned signal 614 is responsive to the sensor signal 612 and may be used to calculate or derive a parameter signal 632.

Further shown in FIG. 6, the signal processor 630 performs signal processing on the conditioned signal 614 to generate the parameter signal 632. The signal processing may include buffering, digital filtering, smoothing, averaging, adaptive filtering and frequency transforms to name a few. The resulting parameter signal 632 may be a measurement calculated or derived from the conditioned signal, such as oxygen saturation, pulse rate, blood glucose, blood pressure and EKG to name a few. Also, the parameter signal 632 may be an intermediate result from which the above-stated measurements may be calculated or derived.

As described above, the sensor interface 610 performs mixed analog and digital pre-processing of an analog sensor signal and provides a digital output signal to the signal processor 630. The signal processor 630 then performs digital post-processing of the front-end processor output. In alternative embodiments, the input sensor signal 612 and the output conditioned signal 614 may be either analog or digital, the front-end processing may be purely analog or purely digital, and the back-end processing may be purely analog or mixed analog or digital.

In addition, FIG. 6 shows an encoder 640, which translates a digital word or serial bit stream, for example, into the baseband signal 642, as is well-known in the art. The baseband signal 642 comprises the symbol stream that drives the transmit signal 654 modulation, and may be a single signal or multiple related signal components, such as in-phase and quadrature signals. The encoder 640 may include data compression and redundancy, also well-known in the art.

FIG. 7 illustrates a monitor module 500 having a receive antenna 770, a receiver 710, a decoder 720, a waveform processor 730 and a monitor interface 750. A receive signal 712 is coupled from the receive antenna 770, which provides wireless communications to a corresponding transmit antenna 670 (FIG. 6), as described above. The receiver 710 inputs the receive signal 712, which corresponds to the transmit signal 654 (FIG. 6). The receiver 710 demodulates the receive signal to generate a baseband signal 714. The decoder 720 translates the symbols of the demodulated baseband signal 714 into a decoded signal 724, such as a digital word stream or bit stream. The waveform processor 730 inputs the decoded signal 724 and generates a constructed signal 732. The monitor interface 750 is configured to communicate the constructed signal 732 to a sensor port 362 of a monitor 360. The monitor 360 may output a sensor drive signal 754, which the monitor interface 750 inputs to the waveform processor 730 as a monitor drive signal 734. The waveform processor 730 may utilize the monitor drive signal 734 to generate the constructed signal 732. The monitor interface 750 may also provide characterization information 758 to the waveform processor 730, relating to the monitor 360, the sensor 310 or both, that the waveform processor 730 utilizes to generate the constructed signal 732.

The constructed signal 732 is adapted to the monitor 360 so that measurements derived by the monitor 360 from the constructed signal 732 are generally equivalent to measurements derivable from the sensor signal 612 (FIG. 6). Note that the sensor 310 (FIG. 6) may or may not be directly compatible with the monitor 360. If the sensor 310 (FIG. 6) is compatible with the monitor 360, the constructed signal 732 is generated so that measurements derived by the monitor 360 from the constructed signal 732 are generally equivalent (within clinical significance) with those derivable directly from the sensor signal 612 (FIG. 6). If the sensor 310 (FIG. 6) is not compatible with the monitor 360, the constructed signal 732 is generated so that measurements derived by the monitor 360 from the constructed signal 732 are generally equivalent to those derivable directly from the sensor signal 612 (FIG. 6) using a compatible monitor.

Wireless Pulse Oximetry

Figure 10:
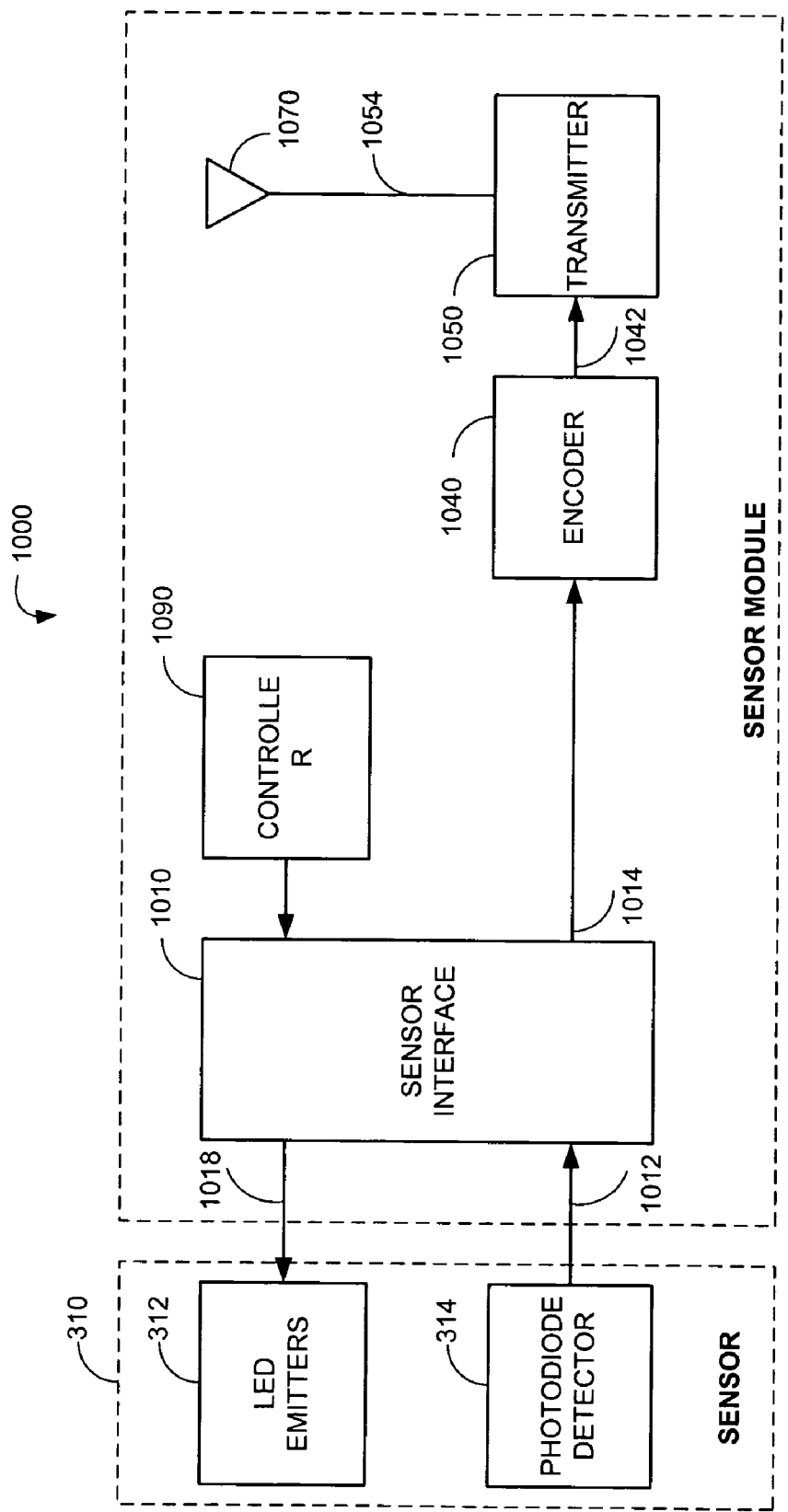
FIG. 10 is a functional block diagram of a sensor module configured to transmit a plethysmograph.
Figure 11:
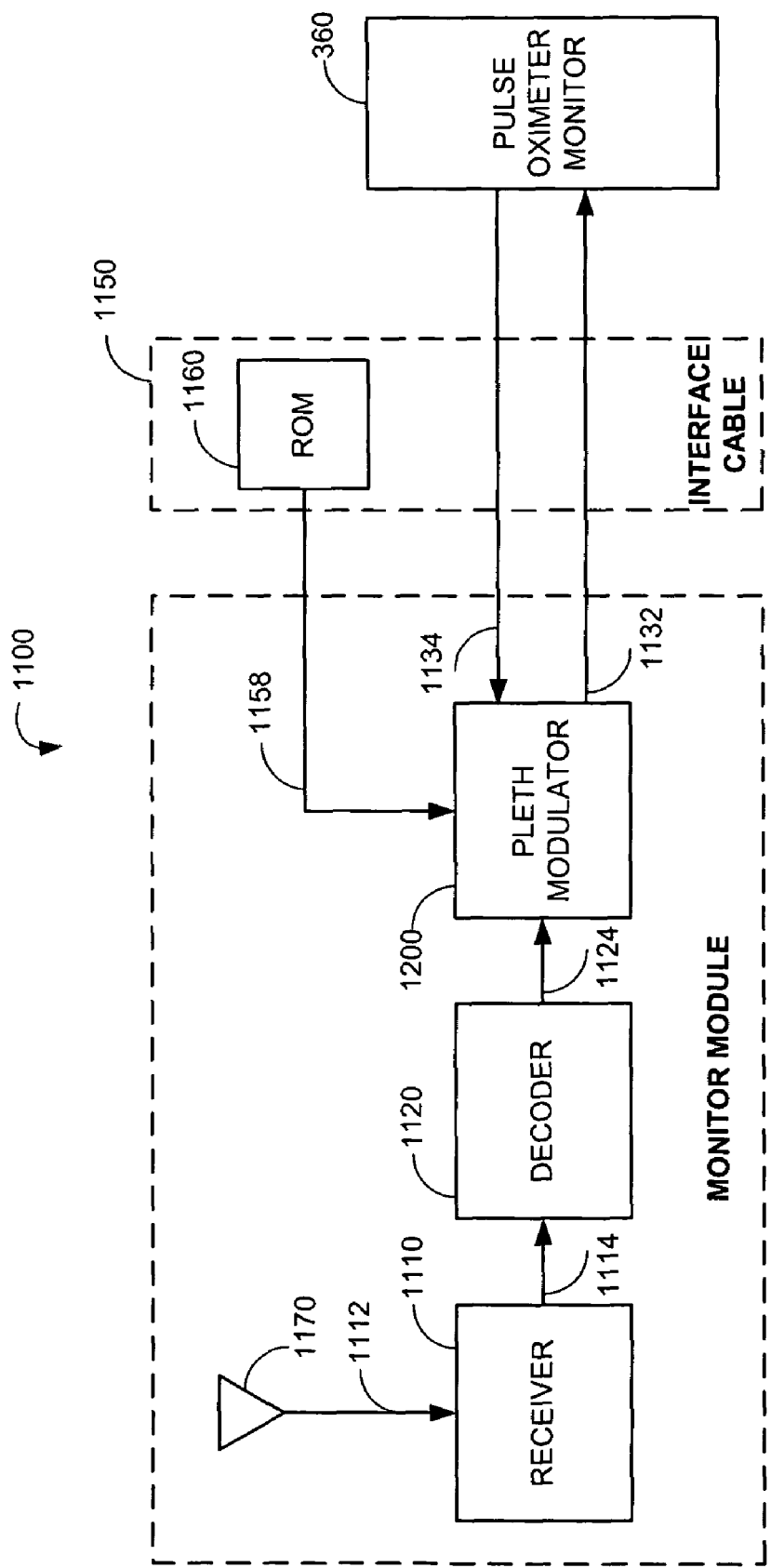
FIG. 11 is a functional block diagram of a monitor module configured to receive a plethysmograph.

FIGS. 8-11 illustrate pulse oximeter embodiments of a communications adapter. FIGS. 8-9 illustrate a sensor module and a monitor module, respectively, configured to communicate measured pulse oximeter parameters. FIGS. 10-11 illustrate a sensor module and a monitor module, respectively, configured to communicate a plethysmograph signal.

Parameter Transmission

Figure 2:
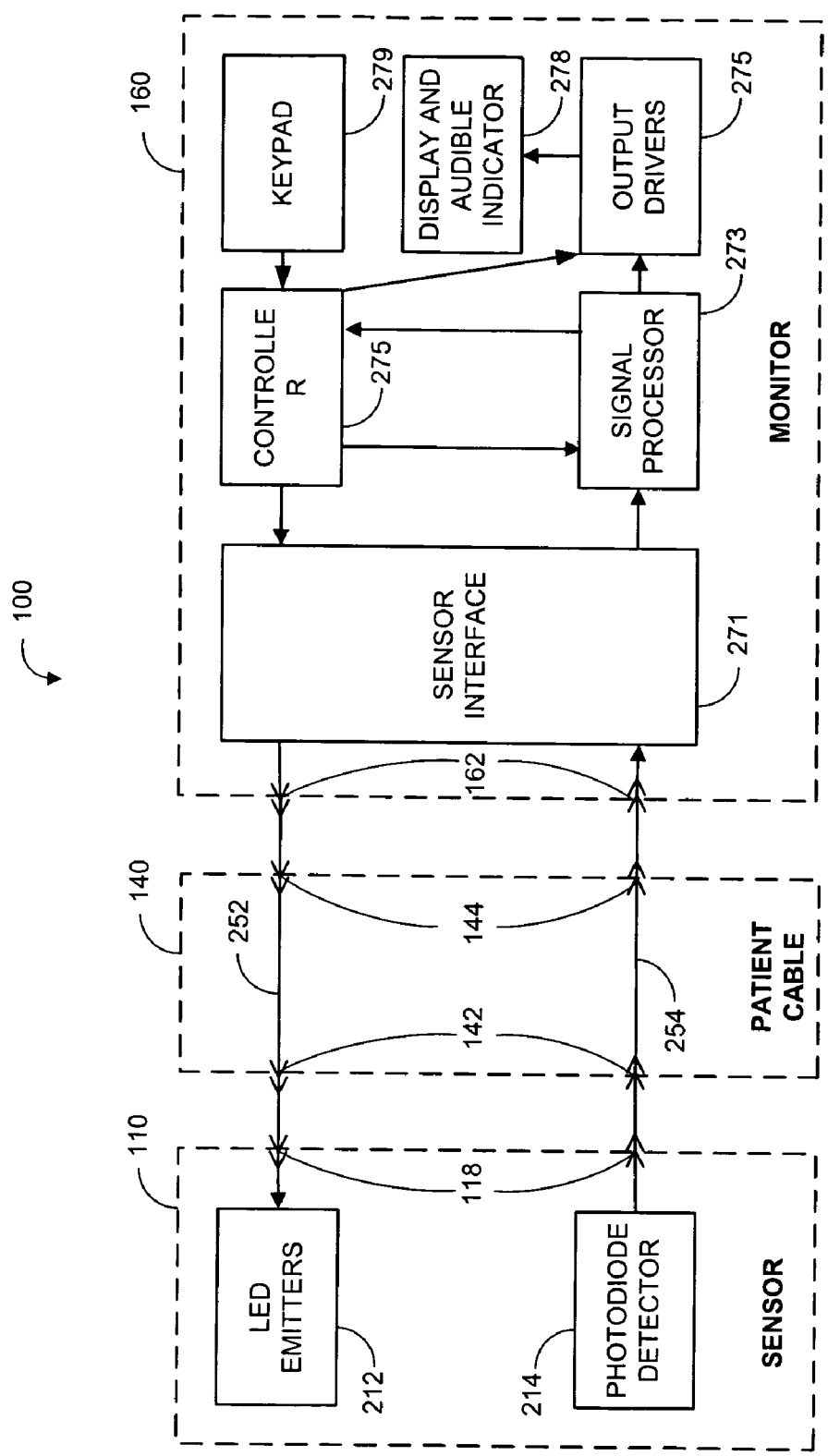
FIG. 2 is a functional block diagram of a prior art pulse oximetry system.

FIG. 8 illustrates a pulse oximetry sensor module 800 having a sensor interface 810, signal processor 830, encoder 840, transmitter 850, transmitting antenna 870 and controller 890. The sensor interface 810, signal processor 830 and controller 890 function as described with respect to FIG. 2, above. The sensor interface 810 communicates with a standard pulse oximetry sensor 310, providing an LED drive signal 818 to the LED emitters 312 and receiving a sensor signal 812 from the detector 314 in response. The sensor interface 810 provides front-end processing of the sensor signal 812, also described above, providing a plethysmograph signal 814 to the signal processor 830. The signal processor 830 then derives a parameter signal 832 that comprises a real time measurement of oxygen saturation and pulse rate. The parameter signal 832 may include other parameters, such as measurements of perfusion index and signal quality. In one embodiment, the signal processor is an MS-5 or MS-7 board available from Masimo Corporation, Irvine, Calif.

As shown in FIG. 8, the encoder 840, the transmitter 850 and the transmitting antenna 870 function as described with respect to FIG. 6, above. For example, the parameter signal 832 may be a digital word stream that is serialized into a bit stream and encoded into a baseband signal 842. The baseband signal 842 may be, for example, two bit symbols that drive a quadrature phase shift keyed (QPSK) modulator in the transmitter 850. Other encodings and modulations are also applicable, as described above. The transmitter 850 inputs the baseband signal 842 and generates a transmit signal 854 that is a modulated carrier having a frequency suitable for short-range transmission, such as within a hospital room, doctor's office, emergency vehicle or critical care ward, to name a few. The transmit signal 854 is coupled to the transmit antenna 870, which provides wireless communications to a corresponding receive antenna 970 (FIG. 9), as described below.

FIG. 9 illustrates a monitor module 900 having a receive antenna 970, a receiver 910, a decoder 920, a waveform generator 930 and an interface cable 950. The receive antenna 970, receiver 910 and decoder 920 function as described with respect to FIG. 7, above. In particular, the receive signal 912 is coupled from the receive antenna 970, which provides wireless communications to a corresponding transmit antenna 870 (FIG. 8). The receiver 910 inputs the receive signal 912, which corresponds to the transmit signal 854 (FIG. 8). The receiver 810 demodulates the receive signal 912 to generate a baseband signal 914. Not accounting for transmission errors, the baseband signal 914 corresponds to the sensor module baseband signal 842 (FIG. 8), for example a symbol stream of two bits each. The decoder 920 assembles the baseband signal 914 into a parameter signal 924, which, for example, may be a sequence of digital words corresponding to oxygen saturation and pulse rate. Again, not accounting for transmission errors, the monitor module parameter signal 924 corresponds to the sensor module parameter signal 832 (FIG. 8), derived by the signal processor 830 (FIG. 8).

Also shown in FIG. 9, the waveform generator 930 is a particular embodiment of the waveform processor 730 (FIG. 7) described above. The waveform generator 930 generates a synthesized waveform 932 that the pulse oximeter monitor 360 can process to calculate $SpO_2$ and pulse rate values or exception messages. In the present embodiment, the waveform generator output does not reflect a physiological waveform. In particular, the synthesized waveform is not physiological data from the sensor module 800, but is a waveform synthesized from predetermined stored waveform data to cause the monitor 360 to calculate oxygen saturation and pulse rate equivalent to or generally equivalent (within clinical significance) to that calculated by the signal processor 830 (FIG. 8). The actual intensity signal from the patient received by the detector 314 (FIG. 8) is not provided to the monitor 360 in the present embodiment. Indeed, the waveform provided to the monitor 360 will usually not resemble a plethysmographic waveform or other physiological data from the patient to whom the sensor module 800 (FIG. 8) is attached.

The synthesized waveform 932 is modulated according to the drive signal input 934. That is, the pulse oximeter monitor 360 expects to receive a red and IR modulated intensity signal originating from a detector, as described with respect to FIGS. 1-2, above. The waveform generator 930 generates the synthesized waveform 932 with a predetermined shape, such as a triangular or sawtooth waveform stored in waveform generator memory or derived by a waveform generator algorithm. The waveform is modulated synchronously with the drive input 934 with first and second amplitudes that are processed in the monitor 360 as red and IR portions of a sensor signal. The frequency and the first and second amplitudes are adjusted so that pulse rate and oxygen saturation measurements derived by the pulse oximeter monitor 360 are generally equivalent to the parameter measurements derived by the signal processor 830 (FIG. 8), as described above. One embodiment of a waveform generator 930 is described in U.S. patent application Ser. No. 60/117,097 entitled "Universal/ Upgrading Pulse Oximeter," assigned to Masimo Corporation, Irvine, Calif. and incorporated by reference herein. Although the waveform generator 930 is described above as synthesizing a waveform that does not resemble a physiological signal, one of ordinary skill will recognize that another embodiment of the waveform generator 930 could incorporate, for example, a plethysmograph simulator or other physiological signal simulator.

Further shown in FIG. 9, the interface cable 950 functions in a manner similar to the monitor interface 750 (FIG. 7) described above. The interface cable 950 is configured to communicate the synthesized waveform 932 to the monitor 360 sensor port and to communicate the sensor drive signal 934 to the waveform generator 930. The interface cable 950 may include a ROM 960 that contains monitor and sensor characterization data. The ROM 960 is read by the waveform generator 930 so that the synthesized waveform 932 is adapted to a particular monitor 360. For example, the ROM 960 may contain calibration data of red/IR versus oxygen saturation, waveform amplitude and waveform shape information. An interface cable is described in U.S. patent application Ser. No. 60/117,092, referenced above. Monitor-specific SatShare™ brand interface cables are available from Masimo Corporation, Irvine, Calif. In an alternative embodiment, such as a direct connect monitor module as illustrated in FIG. 5A, an interface cable 950 is not used and the ROM 960 may be incorporated within the monitor module 900 itself.

Plethysmograph Transmission

FIG. 10 illustrates another pulse oximetry sensor module 1000 having a sensor interface 1010, encoder 1040, transmitter 1050, transmitting antenna 1070 and controller 1090, which have the corresponding functions as those described with respect to FIG. 8, above. The encoder 1040, however, inputs a plethysmograph signal 1014 rather than oxygen saturation and pulse rate measurements 832 (FIG. 8). Thus, the sensor module 1000 according to this embodiment encodes and transmits a plethysmograph signal 1014 to a corresponding monitor module 1100 (FIG. 11) in contrast to derived physiological parameters, such as oxygen saturation and pulse rate. The plethysmograph signal 1014 is illustrated in FIG. 10 as being a direct output from the sensor interface 1010. In another embodiment, the sensor module 1000 incorporates a decimation processor, not shown, after the sensor interface 1010 so as to provide a plethysmograph signal 1014 having a reduced sample rate.

FIG. 11 illustrates another pulse oximetry monitor module 1100 having a receive antenna 1170, a receiver 1110, a decoder 1120 and an interface cable 1150, which have the corresponding functions as those described with respect to FIG. 9, above. This monitor module embodiment 1100, however, has a waveform modulator 1200 rather than a waveform generator 930 (FIG. 9), as described above. The waveform modulator 1200 inputs a plethysmograph signal from the decoder 1120 rather than oxygen saturation and pulse rate measurements, as described with respect to FIG. 9, above. Further, the waveform modulator 1200 provides an modulated waveform 1132 to the pulse oximeter monitor 360 rather than a synthesized waveform, as described with respect to FIG. 9. The modulated waveform 1132 is a plethysmographic waveform modulated according to the monitor drive signal input 1134. That is, the waveform modulator 1200 does not synthesize a waveform, but rather modifies the received plethysmograph signal 1124 to cause the monitor 360 to calculate oxygen saturation and pulse rate generally equivalent (within clinical significance) to that derivable by a compatible, calibrated pulse oximeter directly from the sensor signal 1012 (FIG. 10). The waveform modulator 1200 is described in further detail with respect to FIG. 12, below.

Figure 12:
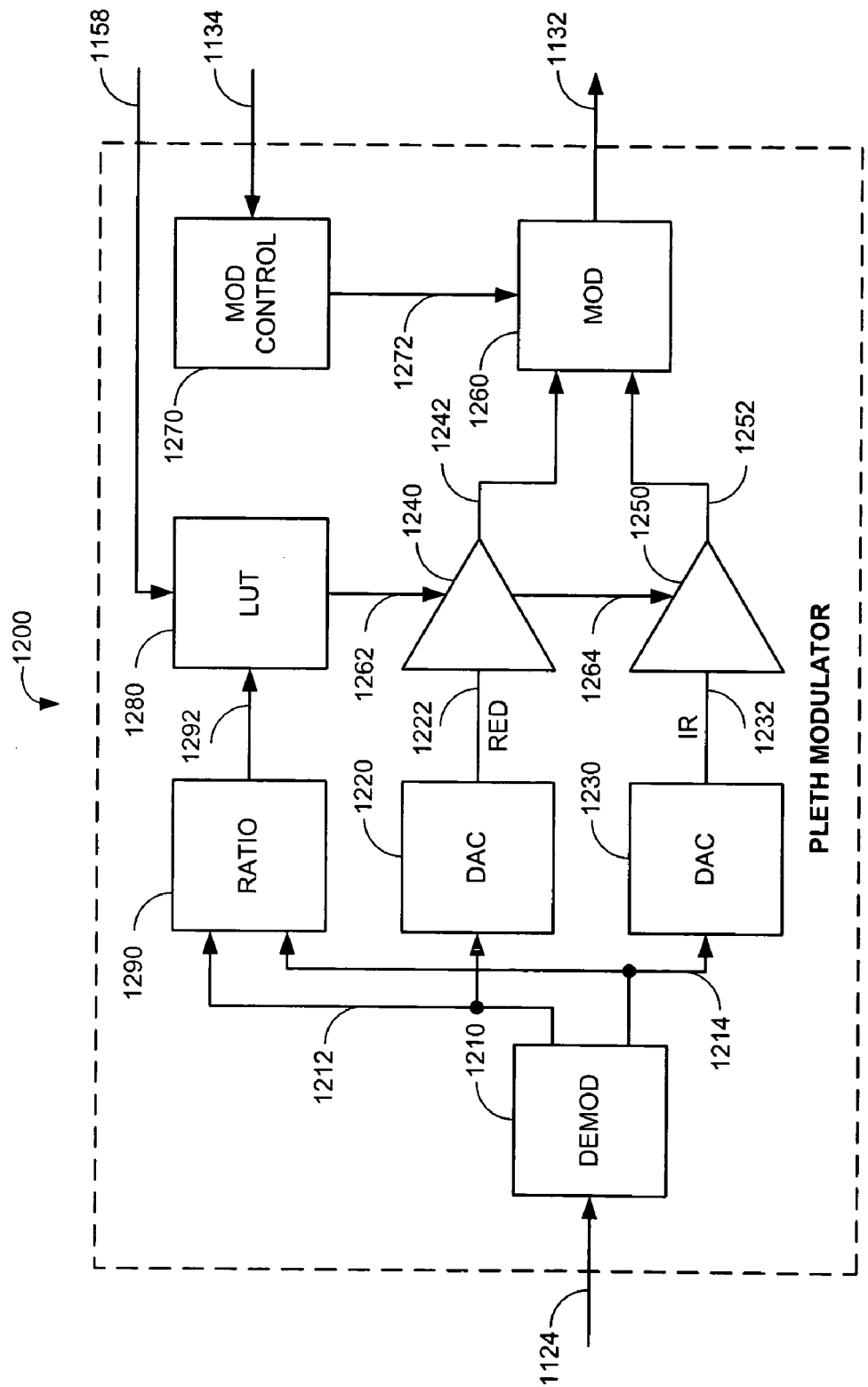
FIG. 12 is a functional block diagram of a waveform modulator.

FIG. 12 shows a waveform modulator 1200 having a demodulator 1210, a red digital-to-analog converter (DAC) 1220, an IR DAC 1230, a red amplifier 1240, an IR amplifier 1250, a modulator 1260, a modulator control 1270, a look-up table (LUT) 1280 and a ratio calculator 1290. The waveform modulator 1200 demodulates red and IR plethysmographs ("pleths") from the decoder output 1124 into a separate red pleth 1222 and IR pleth 1232. The waveform modulator 1200 also adjusts the amplitudes of the pleths 1222, 1232 according to stored calibration curves for the sensor 310 (FIG. 10) and the monitor 360 (FIG. 11). Further, the waveform modulator 1200 re-modulates the adjusted red pleth 1242 and adjusted IR pleth 1252, generating a modulated waveform 1132 to the monitor 360 (FIG. 11).

As shown in FIG. 12, the demodulator 1210 performs the demodulation function described above, generating digital red and IR pleth signals 1212, 1214. The DACs 1220, 1230 convert the digital pleth signals 1212, 1214 to corresponding analog pleth signals 1222, 1232. The amplifiers 1240, 1250 have variable gain control inputs 1262, 1264 and perform the amplitude adjustment function described above, generating adjusted red and IR pleth signals 1242, 1252. The modulator 1260 performs the re-modulation function described above, combining the adjusted red and IR pleth signals 1242, 1252 according to a control signal 1272. The modulator control 1270 generates the control signal 1272 synchronously with the LED drive signal(s) 1134 from the monitor 360.

Also shown in FIG. 12, the ratio calculator 1290 derives a red/IR ratio from the demodulator outputs 1212, 1214. The LUT 1280 stores empirical calibration data for the sensor 310 (FIG. 10). The LUT 1280 also downloads monitor-specific calibration data from the ROM 1160 (FIG. 11) via the ROM output 1158. From this calibration data, the LUT 1280 determines a desired red/IR ratio for the modulated waveform 1132 and generates red and IR gain outputs 1262, 1264 to the corresponding amplifiers 1240, 1250, accordingly. A desired red/IR ratio is one that allows the monitor 360 (FIG. 11) to derive oxygen saturation measurements from the modulated waveform 1132 that are generally equivalent to that derivable directly from the sensor signal 1012 (FIG. 10).

One of ordinary skill in the art will recognize that some of the signal processing functions described with respect to FIGS. 8-11 may be performed either within a sensor module or within a monitor module. Signal processing functions performed within a sensor module may advantageously reduce the transmission bandwidth to a monitor module at a cost of increased sensor module size and power consumption. Likewise, signal processing functions performed within a monitor module may reduce sensor module size and power consumption at a cost of increase transmission bandwidth.

For example, a monitor module embodiment 900 (FIG. 9) described above receives measured pulse oximeter parameters, such as oxygen saturation and pulse rate, and generates a corresponding synthesized waveform. In that embodiment, the oxygen saturation and pulse rate computations are performed within a sensor module 800 (FIG. 8). Another monitor module embodiment 1100 (FIG. 11), also described above, receives a plethysmograph waveform and generates a remodulated waveform. In that embodiment, minimal signal processing is performed within a sensor module 1000 (FIG. 10). In yet another embodiment, not shown, a sensor module transmits a plethysmograph waveform or a decimated plethysmograph waveform having a reduced sample rate. A corresponding monitor module has a signal processor, such as described with respect to FIG. 8, in addition to a waveform generator, as described with respect to FIG. 9. The signal processor computes pulse oximeter parameters and the waveform generator generates a corresponding synthesized waveform, as described above. In this embodiment, minimal signal processing is performed within the sensor module, and the monitor module functions are performed on the pulse oximeter parameters computed within the monitor module.

Wireless Multiple Parameter Measurements

FIGS. 13-14 illustrate a multiple parameter communications adapter. FIG. 13 illustrates a multiple parameter sensor module 1300 having sensor interfaces 1310, one or more signal processors 1330, a multiplexer and encoder 1340, a transmitter 1350, a transmitting antenna 1370 and a controller 1390. One or more physiological sensors 1301 provide input sensor signals 1312 to the sensor module 1300. Depending on the particular sensors 1301, the sensor module 1300 may provide one or more drive signals 1312 to the sensors 1301 as determined by the controller 1390. The sensor interfaces 1310 input the sensor signals 1312 and output one or more conditioned signals 1314. The conditioned signals 1314 may be coupled to the transmitter 1350 or further processed by the signal processors 1330. If the sensor module configuration utilizes signal processors 1330, it derives multiple parameter signals 1332 responsive to the sensor signals 1312, which are then coupled to the transmitter 1350. Regardless, the transmitter 1350 inputs a baseband signal 1342 that is responsive to the sensor signals 1312. The transmitter 1350 modulates the baseband signal 1342 with a carrier to generate a transmit signal 1354, which is coupled to the transmit antenna 1370 and communicated to a corresponding receive antenna 1470 (FIG. 14), as described with respect to FIG. 6, above. Alternatively, there may be multiple baseband signals 1342, and the transmitter 1350 may transmit on multiple frequency channels, where each channel coveys data responsive to one or more of the sensor signals 1314.

As shown in FIG. 13, the sensor interface 1310 conditions and digitizes the sensor signals 1312 as described for a single sensor with respect to FIG. 6, above. The resulting conditioned signals 1314 are responsive to the sensor signals 1312. The signal processors 1330 perform signal processing on the conditioned signals 1314 to derive parameter signals 1332, as described for a single conditioned signal with respect to FIG. 6, above. The parameter signals 1332 may be physiological measurements such as oxygen saturation, pulse rate, blood glucose, blood pressure, EKG, respiration rate and body temperature to name a few, or may be intermediate results from which the above-stated measurements may be calculated or derived. The multiplexer and encoder 1340 combines multiple digital word or serial bit streams into a single digital word or bit stream. The multiplexer and encoder also encodes the digital word or bit stream to generate the baseband signal 1342, as described with respect to FIG. 6, above.

FIG. 14 illustrates a multiple parameter monitor module 1400 having a receive antenna 1470, a receiver 1410, a demultiplexer and decoder 1420, one or more waveform processors 1430 and a monitor interface 1450. The receiver 1410 inputs and demodulates the receive signal 1412 corresponding to the transmit signal 1354 (FIG. 13) to generate a baseband signal 1414 as described with respect to FIG. 7, above. The demultiplexer and decoder 1420 separates the symbol streams corresponding to the multiple conditioned signals 1314 (FIG. 13) and/or parameter signals 1332 (FIG. 13) and translates these symbol streams into multiple decoded signals 1422, as described for a single symbol stream with respect to FIG. 7, above. Alternatively, multiple frequency channels are received to generate multiple baseband signals, each of which are decoded to yield multiple decoded signals 1422. The waveform processors 1430 input the decoded signals 1422 and generate multiple constructed signals 1432, as described for a single decoded signal with respect to FIGS. 7-12, above. The monitor interface 1450 is configured to communicate the constructed signals 1432 to the sensor ports of a multiple parameter monitor 1401 or multiple single parameter monitors, in a manner similar to that for a single constructed signal, as described with respect to FIGS. 7-12, above. In particular, the constructed signals 1432 are adapted to the monitor 1401 so that measurements derived by the monitor 1401 from the constructed signals 1432 are generally equivalent to measurements derivable directly from the sensor signals 1312 (FIG. 13).

A physiological measurement communications adapter is described above with respect to wireless communications and, in particular, radio frequency communications. A sensor module and monitor module, however, may also communicate via wired communications, such as telephone, Internet or fiberoptic cable to name a few. Further, wireless communications can also utilize light frequencies, such as IR or laser to name a few.

A physiological measurement communications adapter has been disclosed in detail in connection with various embodiments. These embodiments are disclosed by way of examples only. One of ordinary skill in the art will appreciate many variations and modifications of a physiological measurement communications adapter within the scope of the claims that follow.

What is claimed is:

1. A communications adapter configured to wirelessly communicate a first signal from a patient site to a remote site and to adapt the first signal to a particular patient monitor at the remote site, the communications adapter comprising:
   a first processor configured to generate said first signal responsive to a sensor signal received from a noninvasive sensor attached to a tissue portion of a patient, wherein said sensor signal is indicative of at least one physiological parameter of a patient;
   a communications link configured to wirelessly transmit the first signal from a first site proximate the patient and to receive the first signal at a second site; and
   a second processor that adapts the first signal to a usually incompatible particular patient monitor at the second site so that the particular patient monitor derives physiological measurements from the adapted first signal that are generally equivalent to measurements derivable from the first signal by a monitor compatible with the noninvasive sensor.

2. The communications adapter according to claim 1 wherein the second processor utilizes (i) measurement data representing a physiological measurement made at the first site, said measurement data transmitted to the second site and (ii) characterization information corresponding to said particular patient monitor that relates predetermined aspects of said first signal to predetermined physiological measurement values that said particular patient monitor would determine when provided with said aspects to generate said adapted first signal adapted to the particular patient monitor.

3. The communications adapter according to claim 2 further comprising: a monitor module housing at least a portion of the communications link and the second processor, the monitor module configured to communicate with a sensor port of the monitor; and a memory associated with the monitor module configured to store the characterization information.

4. The communications adapter according to claim 2 further comprising: a monitor module housing at least a portion of the communications link and the second processor; a cable configured to provide wired communications between the monitor module and a sensor port of the patient monitor; and a memory associated with the cable and configured to store the characterization information.

5. The communications adapter according to claim 2 wherein said second processor adapts said first signal so that said particular patient monitor derives said physiological measurements comprising at least one of oxygen saturation, blood pressure, EKG, respiration rate, body temperature and blood glucose.

6. The communications adapter according to claim 2 wherein said second processor adapts said first signal so that said particular patient monitor derives said physiological measurements comprising at least two of oxygen saturation, blood pressure, EKG, respiration rate, body temperature and blood glucose.

7. The communications adapter according to claim 5 wherein the physiological measurement is oxygen saturation and the first signal is a plethysmograph responsive to at least one of red and IR wavelengths emitted by the noninvasive sensor.

8. A physiological measurement method comprising:
   inputting a sensor signal at a patient location;
   generating a physiological waveform responsive to the sensor signal;
   reducing the sample rate of the physiological waveform;
   wirelessly communicating the reduced sample rate physiological waveform from the patient location to a monitor location;
   adapting the reduced sample rate physiological waveform to a particular patient monitor at the monitor location; and
   outputting the adapted physiological waveform to a sensor port of the patient monitor so that the patient monitor derives physiological measurements from the adapted physiological waveform that are generally equivalent to measurements derivable from the physiological waveform by a monitor compatible with the sensor signal.

9. A communications adapter comprising:

a means for inputting a sensor signal from a noninvasive sensor attached to a patient tissue site;

a means for generating a physiological waveform responsive to the sensor signal;

a means for communicating the physiological waveform from a patient location to a monitor location;

a means for adapting the physiological waveform to a particular monitor at the monitor location; and a means for outputting the adapted physiological waveform to a sensor port of the monitor.

10. The communications adapter according to claim 9 further comprising: a means for relating the adapted physiological waveform and physiological parameter measurements according to the particular monitor.

11. The communications adapter according to claim 10 further comprising a means for reducing the sampling rate of the physiological waveform prior to the wireless communications of the physiological waveform to the monitor location.

* * * * *